(12) United States Patent
Ying et al.

(10) Patent No.: US 9,416,385 B2
(45) Date of Patent: Aug. 16, 2016

(54) METHOD FOR MICROBIAL PRODUCTION OF CYCLIC ADENOSINE 3', 5'-MONOPHOSPHATE

(75) Inventors: Hanjie Ying, Nanjing (CN); Jianxin Bai, Nanjing (CN); He Song, Nanjing (CN); Xiaochun Chen, Nanjing (CN); Jian Xiong, Nanjing (CN); Yong Chen, Nanjing (CN); Jingjing Xie, Nanjing (CN); Jinglan Wu, Nanjing (CN)

(73) Assignee: Nanjing University of Technology, Nanjing (CN)

( * ) Notice: Subject to any disclaimer, the term of this patent is extended or adjusted under 35 U.S.C. 154(b) by 324 days.

(21) Appl. No.: 13/634,513

(22) PCT Filed: Mar. 10, 2011

(86) PCT No.: PCT/CN2011/000382
§ 371 (c)(1),
(2), (4) Date: Nov. 7, 2012

(87) PCT Pub. No.: WO2011/110056
PCT Pub. Date: Sep. 15, 2011

(65) Prior Publication Data
US 2013/0052691 A1 Feb. 28, 2013

(30) Foreign Application Priority Data
Mar. 12, 2010 (CN) .......................... 2010 1 0123134

(51) Int. Cl.
C12P 19/32 (2006.01)
C12N 1/20 (2006.01)
C12N 11/16 (2006.01)

(52) U.S. Cl.
CPC . *C12P 19/32* (2013.01); *C12N 1/20* (2013.01); *C12N 11/16* (2013.01)

(58) Field of Classification Search
CPC ............ C12P 19/32; C12N 1/20; C12N 11/16
See application file for complete search history.

(56) References Cited

U.S. PATENT DOCUMENTS

| 3,827,936 A * | 8/1974 | Shimizu et al. ................. 435/92 |
| 2002/0045568 A1* | 4/2002 | Hotten ................. C07K 14/475 514/8.2 |
| 2004/0086500 A1* | 5/2004 | Bahr ....................... C12N 9/90 424/94.5 |

FOREIGN PATENT DOCUMENTS

| CN | 101230373 A | 7/2008 |
| JP | 52-37073 | 9/1977 |
| JP | 52037073 A * | 9/1977 |

OTHER PUBLICATIONS

Bansal-Mutalik et al. (Enzyme and Microbial Technology, vol. 32, p. 14-26, 2003).*
Ishiyama et al. (JP 52037073 A; English Translation).*
Bansal-Mutalik et al. (Enzyme and Microbial Technology, vol. 32, p. 14-26, 2003.*
Fan et al. J. Biol. Chem. (1995) 270(3): 17723-17729).*
International Preliminary Report on Patentability for Application No. PCT/CN2011/000382, dated Sep. 18, 2012, 17 pages.
Xiao-Chun Chen et al., Medium optimization for the production of cyclic adenosine 3',5'monosphosphate by *Microbacterium* sp. No. 205 using response surface methodology, Biosource Technology 100, Sep. 7, 2008, pp. 919-924.

* cited by examiner

*Primary Examiner* — Susan Hanley
(74) *Attorney, Agent, or Firm* — Lewis Roca Rothgerber Christie LLP

(57) ABSTRACT

The invention relates to a method for the production of adenosine 3',5'-monophosphate (cAMP) by a permeable microbial strain which uses polyols for protecting activities of enzymes and a cAMP precursor and phosphate as substrates. Glucose is used as an energy provider and metal ions and an organic solvent such as acetone are used in the medium.

5 Claims, No Drawings

METHOD FOR MICROBIAL PRODUCTION OF CYCLIC ADENOSINE 3', 5'-MONOPHOSPHATE

CROSS-REFERENCE TO RELATED APPLICATION(S)

This application is a National Phase Patent Application and claims priority to and benefit of International Application Number PCT/CN2011/000382, filed on Mar. 10, 2011, which claims priority to and benefit of Chinese Patent Application Number 201010123134.4, filed on Mar. 12, 2010, the entire disclosure of which are incorporated herein by reference.

TECHNICAL FIELD

The present invention belongs to the field of biocatalysis technology and specifically relates to a method for producing cyclic adenosine monophosphate by whole-cell biocatalysis.

BACKGROUND TECHNOLOGIES

Cyclic adenosine monophosphate is a kind of vital substance with physiological activity, which wildly exists in human body and functions as an intracellular second messenger to play an important role in the synthesis and regulation of carbohydrates, fat metabolism, nucleic acids, proteins and the like. It is used for treating angina pectoris, myocardial infarction, myocarditis, and cardiogenic shock in clinic, has effects on ameliorating symptoms of rheumatic heart disease, such as palpitation, dyspnea, chest distress and the like. It can enhance therapeutic effects of combined chemotherapy on acute leukemia and also can be applied in induced remission of acute leukemia. In addition, it has some therapeutic effects on senile chronic bronchitis, various hepatitis and psoriasis too. Cyclic adenosine monophosphate can also be used to prepare dibutyryl adenosine cyclophosphate and meglumine adenosine cyclophosphate as drug intermediate to increase their solubility in lipid so that they may exert their physiological and pharmacological functions more effectively. Cyclic adenosine monophosphate can be used as food additives for poultry and livestock too where it can simulate roles of growth hormones in vitro to promote growth of poultry and livestock and increase yield of high-quality poultry products.

There are three main methods for preparing cyclic adenosine monophosphate, which are chemical synthesis, fermentation and enzymatic conversion. Currently, all cyclic adenosine monophosphate is prepared by chemical synthesis in foreign and domestic, which uses adenosine monophosphate as starting material, utilizes high performance separation column to separate intermediates, but has complicated operations, huge consumption of solvents, low recovery rate, high cost, and low yield. Fermentation is to incubate microbe cells in minimal medium containing C and N sources with addition of precursor and thereby prepare a large amount of cyclic adenosine monophosphate. But this method has some technical bottlenecks, such as cell membrane permeability, mass transfer of oxygen, environmental coadaptation mechanism and the like, so there is still some distance away from industrialization. Whole-cell biocatalysis is to utilize cyclic adenosine monophosphate synthetase system derived from mammals or microbes (*arthrobacter, Brevibacterium liquefaciens* and the like) to synthesize cyclic adenosine monophosphate. Since cells have the entire multienzyme system for maintaining vital activities and various enzymes retain the original state and particular location in living cells, utilizing microbial cells directly as enzyme source to conduct enzymic catalytic reaction enable multistep enzymic catalytic reaction to be completed rapidly and efficiently and may also cause the step of extracting enzymes from microbial cells to be skipped. This method is attracting more and more researchers' attention due to the features such as high purity of reaction products, simple isolation and purification procedure, short reaction period, pollution-free and the like.

SUMMARY OF THE INVENTION

The technical problem to be resolved by the present invention is to provide a method for producing cyclic adenosine monophosphate by utilizing whole-cell biocatalysis with a decreased cost and easy operation.

The idea of the present invention is: against the defect that enzyme activity is impaired easily during enzymatic reaction, polyhydric organic solvents may be added to protect enzyme activities. Since cells have the entire multienzyme system for maintaining vital activities and various enzymes retain the original state and particular location in living cells, utilizing microbial cells directly as enzyme source to conduct enzymic catalytic reaction enable multistep enzymic catalytic reaction to be completed rapidly and efficiently and may also cause the step of extracting enzymes from microbial cells to be skipped.

To resolve the above-mentioned technical problems, the technical solutions adopted by the present invention are depicted hereinafter:

A method for producing cyclic adenosine monophosphate by whole-cell biocatalysis, using polyhydric organic reagents to protect enzyme activity, cyclic adenosine monophosphate precursor and phosphate ion as substrates, glucose as energy provider, adding metal ions, utilizing permeable microbial strain to prepare cyclic adenosine monophosphate by whole-cell biocatalysis.

Wherein, said polyhydric organic reagents are any one or more reagents selected from mannitol, maltitol, xylitol, lactitol, sorbitol, glycol and glycerol.

Wherein, said cyclic adenosine monophosphate precursor is adenine, adenosine, adenosine monophosphate, adenosine triphosphate, inosine, inosinic acid, or hypoxanthine.

Wherein, said metal ions are any one or more ions selected from magnesium ion and ammonium ion.

Wherein, said microbial strain is any one strain selected from *arthrobacter*, microbacterium, *Brevibacterium liquefaciens, Arthrobacter roseoparaffincus, Escherichia coli, Bacillus subtilis*, yeast, *corynebacterium* and *Brevibacterium ammoniagenes*.

The use amount of yeast cells is 10~1,000 g wet yeast/L, preferably 200~600 g/L, i.e. as for the reaction solution with a total volume of 1 L, 10~1,000 g of wet yeast, preferably 200~600 g of wet yeast should be added.

The use forms of yeast are dried yeasts, cells obtained by fermentation culture, isolation and centrifugation, immobilized cells, lyophilized cells, yeast powder sold in the market, air dried yeast or waste yeast paste.

Wherein, the permeable microbial strain refers to producing microbial strain where permeability of the cell membrane is changed by chemical, physical or biological treatments and concrete method is surfactant method, organic solvent method, freeze-thaw method, ultrasonic wave treatment, air drying, freeze drying or lysozyme method.

Surfactant used in the surfactant method is nonionic surfactant polyethylene oxide amine or Triton X-100, cationic surfactant cetyltrimethyl ammonium bromide, or anionic surfactant lauroyl sarcosinate. The use amount of surfactant is 0.01~50 g/L, preferably 1~20 g/L, which means that when treating producing strain by surfactant method, surfactant is added into the reaction solution directly, 0.01~50 g, preferably 1~20 g shall be added as for the reaction solution with the total volume of 1 L.

Organic solvent used in the organic solvent method is xylene, toluene, fatty alcohol, acetone, or ethyl acetate and concentration of organic solvent is 0.01~50 mL/L, preferably 1~20 mL/L, which means that treating producing strain by the organic solvent method, organic solvent is added into the reaction solution directly and 0.01~50 mL, preferably 1~20 mL shall be added as for the reaction solution with the total volume of 1 L.

As for other methods for treating permeability of cells, such as freeze-thaw method, ultrasonic wave treatment, air drying and the like, the way of treating strain cells firstly followed by adding the treated strain into the reaction solution is adopted.

Initial reaction concentration of polyhydric organic solvent is 0.001~10 g/L, initial reaction concentration of cyclic adenosine monophosphate precursor is 0.01~100 g/L, initial reaction concentration of phosphate ion is 0.01~100 g/L, initial reaction concentration of glucose is 0.01~100 g/L, initial reaction concentration of metal ion is 0.001~10 g/L, use amount of microbial strain is 10~1,000 g wet thallus/L. Preferably, initial reaction concentration of polyhydric organic solvent is 0.5~1.5 g/L, initial reaction concentration of cyclic adenosine monophosphate precursor is 2~15 g/L, initial reaction concentration of phosphate ion is 5~20 g/L, initial reaction concentration of glucose is 50~80 g/L, initial reaction concentration of metal ion is 2~7 g/L, use amount of microbial strain is 20~1,000 g wet thallus/L.

The above-mentioned synthesis reaction of cyclic adenosine monophosphate is conducted in aqueous solution for 2~200 hours under the condition of pH 4~10 and 25~38° C., preferably for 5~20 hours under the condition of pH 6~8 and 28~35° C.

The beneficial effects of the present invention are as follows:

1. A great number of research experiences show that addition of polyhydric organic solvent may increase chemical potential of enzymes and thus more free energy is required for damaging structure of the enzyme, which results in a more stable conformation of the enzyme so as to protect activity of the enzyme on the other hand.

2. In comparison with enzyme catalysis, since the present invention adopts whole cells, intracellular enzymes are protected by cell walls/membranes and thereby have better stability and longer half-life, which facilitates regeneration of energy and co-enzymes; the existence of intracellular various enzyme systems may achieve a cascade of enzymatic reaction, which remedies the deficiency of enzyme catalysis that cascade reactions are difficult to realize; purification of enzymes are skipped in the meanwhile; the preparation method is simple and low-lost.

3. Pre-treatment on microbes improves permeability of microbial cell walls, which accelerates diffusion and permeation of reacting components into microbial cells, facilitates exposure of substrates to enzyme system, and thereby shortens the time of appearance of maximum conversion rate and maximum yield rate to some extent.

EMBODIMENTS OF THE INVENTION

The present invention may be better understood based on the examples hereinafter. However, it is understood easily by those skilled in the art that the particular ratios of materials, the technical conditions, and the results as depicted in the examples are only used for illustration of the present invention, but do not intend to or shall not limit the present invention as described in details in the claims.

Example 1

Culture medium of microbial strain: glucose 50 g/L, urea 2.0 g/L, potassium dihydrogen phosphate 5.0 g/L, magnesium sulfate 0.5 g/L, biotin $0.05 \times 10^{-3}$ g/L.

Inoculation amount of microbial strain was 10%. The inoculated medium was incubated on a shaking table at 30° C. and 120 rpm for 24 hours. The culture was centrifuged at 8,000 rpm for 10 minutes. The bacterial sludge was collected and preserved at −10° C. for use.

Example 2

Synthesis of Cyclic Adenosine Monophosphate from Hypoxanthine

In a 500 ml beaker, 300 ml of reaction solution was prepared, consisting of 4 g/L hypoxanthine, 50 g/L glucose, 100 g *arthrobacter* sludge, 8 g/L potassium dihydrogen phosphate, 1 g/L $MgSO_4$, 1 g/L $NH_4Cl$, 4.5 ml toluene, 0.5 g/L mannitol, 0.5 g/L xylitol and water, and then pH was adjusted to 6.5 with sodium hydroxide. The reaction was conducted at 30° C. while stirring at low speed for 8 hours. After the reaction was stopped, the solution was precipitated with 40% trichloroacetic acid. Quantitative analysis of cyclic adenosine monophosphate using HPLC showed the conversion solution contained 4.5 g/L of cyclic adenosine monophosphate.

Example 3

Synthesis of Cyclic Adenosine Monophosphate from Adenosine

In a 500 ml beaker, 300 ml of reaction solution was prepared, consisting of 6 g/L adenosine, 60 g/L glucose, 120 g air dried Microbacterium sludge, 10 g/L potassium dihydrogen phosphate, 10 g/L dipotassium phosphate, 0.5 g/L $MgCl_2$, 2 g/L $NH_4Cl$, 1 g/L glycerol, 1 g/L mannitol and water, and then pH was adjusted to 7.0 with sodium hydroxide. The reaction was conducted at 33° C. while stirring at low speed for 6 hours. After the reaction was stopped, the solution was precipitated with 40% trichloroacetic acid. Quantitative analysis of cyclic adenosine monophosphate using HPLC showed the conversion solution contains 3.5 g/L of cyclic adenosine monophosphate.

Example 4

Synthesis of Cyclic Adenosine Monophosphate from Adenine

In a 500 ml beaker, 300 ml of reaction solution was prepared, consisting of 10 g/L adenine, 50 g/L glucose, 300 g *Brevibacterium liquefaciens*, 5 g/L disodium phosphate, 2 g/L $MgCl_2$, 2 g/L $NH_4Cl$, 0.3 ml acetone, 1 g/L glycerol and water, and then pH was adjusted to 7.5 with potassium hydroxide. The reaction was conducted at 32° C. while stirring at low speed for 5 hours. After the reaction was stopped, the solution was precipitated with 40% trichloroacetic acid. Quantitative analysis of cyclic adenosine monophosphate using HPLC showed the conversion solution contains 3.2 g/L of cyclic adenosine monophosphate.

Example 5

Synthesis of Cyclic Adenosine Monophosphate from Adenosine Monophosphate

In a 500 ml beaker, 300 ml of reaction solution was prepared, consisting of 10 g/L adenosine monophosphate, 70 g/L glucose, 60 g *corynebacterium* sludge, 7 g/L disodium phosphate, 3 g/L $MgCl_2$, 1 g/L $NH_4Cl$, 15 ml acetone, 0.6 g/L glycerol and water, and then pH was adjusted to 8 with potassium hydroxide. The reaction was conducted at 28° C. while stirring at low speed for 20 hours. After the reaction was stopped, the solution was precipitated with 40% trichloroacetic acid. Quantitative analysis of cyclic adenosine monophosphate using HPLC showed the conversion solution contains 1.2 g/L of cyclic adenosine monophosphate.

Example 6

Synthesis of Cyclic Adenosine Monophosphate from Adenosine Triphosphate

In a 500 ml beaker, 300 ml of reaction solution was prepared, consisting of 12 g/L adenosine triphosphate, 80 g/L glucose, 180 g *arthrobacter* sludge, 5 g/L disodium phosphate, 2 g/L $MgCl_2$, 5 g/L $NH_4Cl$, 0.03 g cationic surfactant cetyltrimethyl ammonium bromide, 1.5 g/L glycerol and water, and then pH was adjusted to 6.5 with potassium hydroxide. The reaction was conducted at 31° C. while stirring at low speed for 10 hours. After the reaction was stopped, the solution was precipitated with 40% trichloroacetic acid. Quantitative analysis of cyclic adenosine monophosphate using HPLC showed the conversion solution contains 4.0 g/L of cyclic adenosine monophosphate.

Example 7

Synthesis of Cyclic Adenosine Monophosphate from Inosine

In a 500 ml beaker, 300 ml of reaction solution was prepared, consisting of 6 g/L inosine, 80 g/L glucose, 80 g *Brevibacterium ammoniagenes,* 6 g/L disodium phosphate, 5 g/L $MgCl_2$, 2 g/L $NH_4Cl$, 1.5 g anionic surfactant lauroyl sarcosinate, 1 g/L glycerol and water, and then pH was adjusted to 7 with potassium hydroxide. The reaction was conducted at 34° C. while stirring at low speed for 18 hours. After the reaction was stopped, the solution was precipitated with 40% trichloroacetic acid. Quantitative analysis of cyclic adenosine monophosphate using HPLC showed the conversion solution contains 1.2 g/L of cyclic adenosine monophosphate.

The invention claimed is:

1. A method for producing cyclic adenosine monophosphate by whole-cell biocatalysis, the method comprising:
preparing a reaction solution comprising an enzyme activity protector, a substrate, an energy provider, a metal ion, and a permeable microbial strain and an organic solvent; and
conducting a whole-cell biocatalysis reaction in said reaction solution to obtain cyclic adenosine monophosphate,
wherein said enzyme activity protector is one or more polyhydric organic reagents selected from the group consisting of mannitol, maltitol, xylitol, lactitol, sorbitol, and glycol; said substrate comprises a cyclic adenosine monophosphate precursor and phosphate ion; and said energy provider is glucose; said metal ions are any one or more selected from magnesium ion and ammonium ion; said permeable microbial strain is any one strain selected from *arthrobacter*, microbaterium and *corynebacterium*; and said organic solvent is acetone;
wherein the one or more polyhydric organic reagents is present in an initial reaction concentration of 0.001-10 g/L, the cyclic adenosine monophosphate precursor is present in an initial reaction concentration of 0.01-100 g/L, the phosphate on is present in an initial reaction concentration of 0.01-100 g/L, the glucose is present in an initial reaction concentration of 0.01-100 g/L, the metal ion is present in an initial reaction concentration of 0.001-10 g/L, the microbial strain is present in an amount of 10-1,000 g wet thallus/L, and the acetone is present in an initial reaction concentration of 0.01-50 mL/L.

2. The method for producing cyclic adenosine monophosphate by whole-cell biocatalysis according to claim 1, characterized in that said cyclic adenosine monophosphate precursor is adenine, adenosine, adenosine monophosphate, adenosine triphosphate, inosine, inosinic acid, or hypoxanthine.

3. The method for producing cyclic adenosine monophosphate by whole-cell biocatalysis according to claim 1, characterized in that the conducting a whole-cell biocatalysis reaction is conducted in aqueous solution for 2-200 hours under the condition of pH 4-10 and 25-38° C.

4. The method for producing cyclic adenosine monophosphate by whole-cell biocatalysis according to claim 2, characterized in that the conducting a whole-cell biocatalysis reaction is conducted in aqueous solution for 2-200 hours under the condition of pH 4-10 and 25-38° C.

5. The method for producing cyclic adenosine monophosphate by whole-cell biocatalysis according to claim 1, characterized in that said microbial strain is any one strain selected from *Brevibacterium liquefaciens, Arthrobacter roseoparaffincus, Escherichia coli, Bacillus subtilis*, yeast and *Brevibacterium ammoniagenes*.

* * * * *